US006514768B1

(12) United States Patent
Guire et al.

(10) Patent No.: US 6,514,768 B1
(45) Date of Patent: *Feb. 4, 2003

(54) REPLICABLE PROBE ARRAY

(75) Inventors: Patrick E. Guire, Eden Prairie, MN (US); Melvin J. Swanson, Carver, MN (US)

(73) Assignee: Surmodics, Inc., Eden Prairie, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/240,466

(22) Filed: Jan. 29, 1999

(51) Int. Cl.[7] .............................................. C07H 21/04

(52) U.S. Cl. ..................... 436/518; 536/22.1; 536/25.3; 536/25.32; 536/23.1; 536/24.3; 435/6; 435/7.1; 435/7.92; 435/7.94; 435/7.95; 435/DIG. 45; 436/527; 436/807; 436/809

(58) Field of Search ............................... 536/22.1, 24.3, 536/25.3, 25.32, 23.1; 435/6, 7.1, 7.92, 7.94, 7.95, DIG. 45; 436/518, 527, 807, 809

(56) References Cited

U.S. PATENT DOCUMENTS

| 4,722,906 A | 2/1988 | Guire ......................... 436/501 |
| 4,979,959 A | 12/1990 | Guire ......................... 623/66 |
| 5,002,582 A | 3/1991 | Guire et al. ................... 623/66 |
| 5,217,492 A | 6/1993 | Guire et al. ................... 623/11 |
| 5,445,934 A | 8/1995 | Fodor et al. .................... 435/6 |
| 5,512,329 A | 4/1996 | Guire et al. ................. 427/508 |
| 5,563,056 A | 10/1996 | Swan et al. .................. 435/180 |
| 5,587,293 A | * 12/1996 | Kauvar et al. ................ 435/7.9 |
| 5,637,460 A | 6/1997 | Swan et al. ..................... 435/6 |
| 5,700,637 A | 12/1997 | Southern ....................... 435/6 |
| 5,714,360 A | 2/1998 | Swan et al. ................... 435/174 |
| 5,744,305 A | 4/1998 | Fodor et al. .................... 435/6 |
| 5,770,722 A | 6/1998 | Lockhart et al. ............ 536/25.3 |
| 5,795,714 A | 8/1998 | Cantor et al. ................... 435/6 |
| 5,837,832 A | 11/1998 | Chee et al. ................. 536/22.1 |
| 5,900,481 A | 5/1999 | Lough et al. ............... 536/55.3 |
| 6,057,100 A | 5/2000 | Heyneker |

FOREIGN PATENT DOCUMENTS

| WO | WO 92/10092 | 6/1992 |
| WO | WO 93/17126 | 9/1993 |
| WO | WO 96/01836 | 1/1996 |
| WO | PCT/US96/07695 | 11/1996 |
| WO | PCT/US96/08797 | 12/1996 |
| WO | WO 97/06468 | 2/1997 |
| WO | WO 97/31236 | 8/1997 |
| WO | PCT/US97/05344 | 9/1997 |
| WO | WO 98/09735 | 3/1998 |
| WO | WO 98/14610 | 4/1998 |
| WO | WO 98/20019 | 5/1998 |
| WO | WO 00/27521 | 5/2000 |

OTHER PUBLICATIONS

Borman, S., "Reducing Time To Drug Discovery", *Chemical and Engineering News*, vol. 77, No. 10, pp. 10 pgs. (Mar. 8, 1999).
Ferguson, J. et al., "A fiber–optic DNA biosensor microarray for analysis of gene expression", *Nature Biotechnology*, vol. 14, No. 13, pp 1681–1684 (Dec. 1996).
Healey, B. et al., "Fiberoptic DNA Senosor Array Capable of Detecting Point Mutations", *Analytical Biochemistry*, vol. 251, pp. 270–279, (1997).
Luther, A. et al., "Surface–promoted replication and exponential amplification of DNA analogues", *Letters to Nature*, vol. 396, pp. 245–248 (Nov. 19, 1998).
Walt, D., "Fiber Optic Imaging Sensors", *Accounts of Chemical Research*, vol. 31, No. 5, pp. 267–278 (1998).
Oakeley et al., "Changing Functionality of Surfaces by Directed Self–Assembly Using Oligonucleotides—The Oligo–Tag", BioTechniques 27:752–760 (Oct. 1999).
Gerry et all., "Universal DNA Microarray Method for Multiplex Detection of Low Abundance Point Mutations", J. Mol. Biol. 292:251–2262 (1999).
Nucleic Acid Hyrbridization: A Practical Approach, Hames and Higgins, eds., 1985, pp. 3–15, 62–66 and 73–112.
Stipp, D., "Gene Chip Breakthrough", Fortune, p. 56–73, Mar. 31, 1997.
Borman, S., "DNA Chips Come of Age", C&EN, p. 42–43 Dec. 9, 1996.
Travis, J., "Chips Ahoy", Science News 151:144–145 (1997).
Service, R., "Microchip Arrays Put DNA on the Spot", Science 282(5388):396–399, Oct. 16, 1998.
Amato, I., "Fomenting a Revolution, in Miniature", Science 282(5388): 402–405, Oct. 16, 1998.
Lipshutz, R.J., et al., "Using Oligonucleotide Probe Arrays to Access Genetic Diversity", BioTechniques 19(3):442–447 (1995).
Heller, R.A., et al., "Discovery and analysis of inflammatory disease–related genes using cDNA microarrays", Proc. Natl. Acad. Sci. USA, 94:2150–2155 (1997).
Michael, K., et al., "Randomly Ordered Addressable High –Density Optical Sensor Arrays", Analytical Chem. 70(7):1242 (1998).

* cited by examiner

*Primary Examiner*—Padmashri Ponnaluri
(74) *Attorney, Agent, or Firm*—Merchant & Gould P.C.

(57) ABSTRACT

A system for producing substantially identical specific binding ligand (e.g., nucleic acid) probe arrays, for instance, by preparing and replicating an original master array and/or by providing a reusable assay array that is capable of being regenerated. In one embodiment the system includes the preparation and use of a) a master array surface having address sequences immobilized in the form of a patterned, and optionally random, array, b) a multi-ligand conjugate having a binding domain complementary to an address sequence, a binding domain complementary to a target sequence, and a third ligand for use in forming (e.g., by binding or polymerization) the conjugates into or onto the surface of assay array, which can be used with or upon disassociation of the address and its complementary sequences.

15 Claims, 4 Drawing Sheets

REPLICABLE PROBE ARRAY

TECHNICAL FIELD

The present invention relates to the immobilization of specific binding ligands, such as nucleic acids and other ligands, in a known spatial arrangement. In another aspect, the invention relates to solid supports, such as oligonucleotide chips, incorporating such nucleic acids. In yet another aspect, the invention relates to photoreactive groups, to molecules and/or surfaces derivatized with such groups, and to the attachment of such molecules to support surfaces by the activation of such groups.

BACKGROUND OF THE INVENTION

The development of oligonucleotide probe arrays, more commonly known as "DNA chips" and GENE CHIP (a registered trademark of Affymetrix, Inc.), has made significant advances over the past few years, and is becoming the center of ever-increasing attention and heightened significance. See, for instance, Stipp, D., *Fortune, p.*56, Mar. 31, 1997. See also Borman, S., *C&EN,* p.42, Dec. 9, 1996, and Travis, J., *Science News* 151:144–145 (1997). These 2- or 3-cm square chips are capable of containing tens of thousands to hundreds of thousands of immobilized oligonucleotides, allowing researchers to witness for the first time the behavior of thousands of genes acting in concert. DNA chips are useful for observing unique gene expression patterns, gauging the success of drug treatment, tailoring medications to patients based upon their genetic makeup, sequencing genes, and conducting research in the area of genetic medicine. See also, "Microchip Arrays Put DNA on the Spot", R. Service, *Science* 282(5388):396–399, Oct. 16, 1998; and "Fomenting a Revolution, in Miniature", I. Amato, *Science* 282(5388): 402–405, Oct. 16, 1998.

Typically, oligonucleotide probe arrays display specific oligonucleotide sequences at precise locations in an information rich format. In use, the hybridization pattern of a fluorescently labeled nucleic acid target is used to gain primary structure information for the target. This format can be applied to a broad range of nucleic acid sequence analysis problems including pathogen identification, forensic applications, monitoring mRNA expression and de novo sequencing. See, for instance, Lipshutz, R. J., et al., *Bio-Techniques* 19(3):442–447 (1995). Such arrays sometimes need to carry several tens of thousands, or even hundreds of thousands of individual probes. The chips also need to provide a broad range of sensitivities in order to detect sequences that can be expressed at levels anywhere from 1 to 10,000 copies per cell.

A variety of approaches have been developed for the fabrication and/or use of oligonucleotide probe arrays. See, for instance, Weaver, et al. (WO 92/10092) which describes a synthetic strategy for the creation of large scale chemical diversity on a solid-phase support. The system employs solid-phase chemistry, photolabile protecting groups and photolithography to achieve light-directed, spatially addressable, parallel chemical synthesis. Using the proper sequence of masks and chemical stepwise reactions, a defined set of oligonucleotides can be constructed, each in a predefined position on the surface of the array.

Using this technology, Affymetrix, Inc. (Santa Clara, Calif.), has developed libraries of unimolecular, double-stranded oligonucleotides on a solid support. See, for instance, U.S. Pat. No. 5,770,722 which describes arrays containing oligonucleotides from 4 to 100 nucleotides in length. The arrays comprise a solid support, an optional spacer, a first oligonucleotide, a second oligonucleotide that is complementary to the first, and a flexible linker or probe. The libraries described are useful for screening for such receptors as proteins, RNA or other molecules which bind double-stranded DNA. Another array developed by Affymetrix is described in U.S. Pat. No. 5,837,832. This reference describes methods for making high-density arrays of oligonucleotide probes on silica chips. The oligonucleotide probes are 9 to 20 nucleotides in length and are synthesized directly on a solid support. The arrays comprise oligonucleotide probes that are complementary to a section of the reference sequence.

Synteni (Palo Alto, Calif.) produces arrays of cDNA by applying polylysine to glass slides, followed by printing cDNA onto the coated slides. The arrays are then exposed to UV light, in order to crosslink the DNA with the polylysine. Unreacted polylysine is then blocked by reaction with succinic anhydride. These arrays, called "Gene Expression Microarrays" (GEM™) are used by labeling mRNA prepared from a normal cell with a fluorescent dye, then labeling mRNA from an abnormal cell with a fluorescent dye of a different color. These two labeled mRNA molecules are simultaneously applied to the microarray, where they competitively bind to the immobilized cDNA molecules. This two color coding technique is used to identify the differences in gene expression between two cell samples. (Heller, R. A., et al., *Proc. Natl. Acad. Sci. USA,* 94:2150–2155 (1997)).

At least one group, Cantor, et al. (U.S. Pat. No. 5,795,714), describes methods for replicating arrays of probes which are said to be useful for the large scale manufacture of diagnostic aids. The patent includes a method for replicating an array of single-stranded probes on a solid support comprising the steps of:

a) synthesizing an array of nucleic acids each comprising a non-variant sequence of length C at a 3'-terminus and a variable sequence of length R at a 5'-terminus;

b) fixing the array to a first solid support;

c) synthesizing a set of nucleic acids each comprising a sequence complementary to the non-variant sequence;

d) hybridizing the nucleic acids of the set to the array;

e) enzymatically extending the nucleic acids of the set using the variable sequences of the array as templates;

f) denaturing the set of extended nucleic acids; and g) fixing the denatured nucleic acids of the set to a second solid support to create the replicated array of single-stranded probes.

On a separate subject, the assignee of the present invention has previously described a variety of applications for the use of photochemistry, and in particular, photoreactive groups, e.g., for attaching polymers and other molecules to support surfaces. See, for instance, U.S. Pat. Nos. 4,722,906, 4,979,959, 5,217,492, 5,512,329, 5,563,056, 5,637,460, and 5,714,360 and International Patent Application Nos. PCT/US96/08797 (Virus Inactivating Coatings), PCT/US96/07695 (Capillary Endothelialization), and PCT/US97/05344 (Chain Transfer Agents).

In spite of the various developments to date, there remains a need for methods and reagents that improve the immobilization of nucleic acids onto a variety of support materials, e.g., in order to form oligonucleotide probe arrays. What is clearly needed are new and improved methods and reagents for reproducibly preparing specific binding ligand (e.g., nucleic acid) arrays in a cost-effective and efficient manner, while maintaining an accurate, sensitive product.

SUMMARY OF THE INVENTION

The present invention, in one preferred embodiment, provides a system for producing substantially identical specific binding ligand (e.g., nucleic acid) probe arrays, for instance, by preparing and replicating an original "master" array and/or by providing a reusable assay array that is capable of being regenerated. The present approach can be contrasted with the traditional approach of separately and individually preparing each probe array anew, without the efficiency of replicating a master array or the flexibility of regenerating an array for subsequent use. The present method can be adapted for use with conventional arrays, in order to provide replicates thereof, but is preferably used with a master array (and other components) specifically designed for such purposes, in the manner described herein.

In such a preferred embodiment, the present invention provides a method and system for reproducibly preparing an assay array, the system comprising:

a) a master array comprising a support surface having a plurality of "address" ligands (e.g., oligonucleotide sequences) immobilized thereon, for instance, directly or via respective linking agents, such as "micro-beads" or other suitable linkers, the ligands being immobilized in the form of a patterned, and optionally random, array;

b) a plurality of multi-ligand conjugates, each multi-ligand conjugate comprising a core (e.g., molecular or solid) having (preferably independently) attached thereto: (i) at least one molecule of a first ligand (e.g., oligonucleotide) binding domain, comprising a ligand selected to bind in a complementary manner to a particular address ligand of the master array, (ii) at least one molecule of a second ligand (e.g., oligonueleotide) binding domain, comprising a ligand selected to bind in a complementary manner to a characteristic ligand of a target nucleic acid sequence (e.g., a gene and/or gene fragment), and (iii) at least one molecule of a third (and preferably non-oligonucleotide) ligand, selected from the group consisting of binding ligands and polymerizable groups (e.g., acrylic or vinyl groups); and c) an assay array support comprising a support surface for the replicate array, e.g., coated with attachment sites for the third ligand (such as, immobilized molecules of a corresponding binding partner specific for the third ligand).

A corresponding preferred method of the invention, wherein the address and target ligands are both nucleic acids, preferably oligonucleotides, involves the steps of: (1) providing a master array as described above, (2) attaching the multi-ligand conjugates thereto, by allowing their respective oligonucleotide binding domains to hybridize to the complementary address sequences of the master array, (3) bringing the assay array support into sufficient proximity with the master array, under conditions suitable to permit the attached multi-ligand conjugates to attach to the assay array support (e.g., by binding between the third ligands and the corresponding attachment sites present upon the assay support surface), and (4) disassociating the hybridized complementary oligonucleotides under conditions suitable to permit the assay array support to be recovered and used. The resulting assay array comprises an assay array support having attached thereto a plurality of multi-ligand conjugates (preferably still having complementary target oligonucleotides thereon) present in a pattern established by the master array.

In an alternative preferred embodiment, where the conjugate includes a polymerizable group (e.g., in addition to the third binding ligand, or in place of the third binding ligand), the multi-ligand conjugates can be maintained in their oriented positions upon the master array surface by polymerizing those groups in situ, in order to form a polymeric backing sufficient to permit the resultant polymerized layer to be supported and used, e.g., transferred to an assay array support, while retaining the spatial arrangement established by the master array addresses.

Once transferred to an assay array support, the second oligonucleotide binding domains, in turn, can be used in a conventional manner to determine the presence (e.g., in absolute or relative amounts) of one or more target nucleic acids in a sample. The order and arrangement of the second binding domains is predetermined and maintained in the course of the replicating method set forth herein. For instance, the resultant assay array can be used in a conventional manner, e.g., by contacting the array with a sample suspected of containing the target nucleic acid, under conditions suitable to permit any target nucleic acid to be hybridized and detected.

In other aspects, the invention provides a method of using such a system; the various components for use in such a system, including a kit or combination of one or more components; as well as an assay array formed by the method of the invention.

Figure 1A:
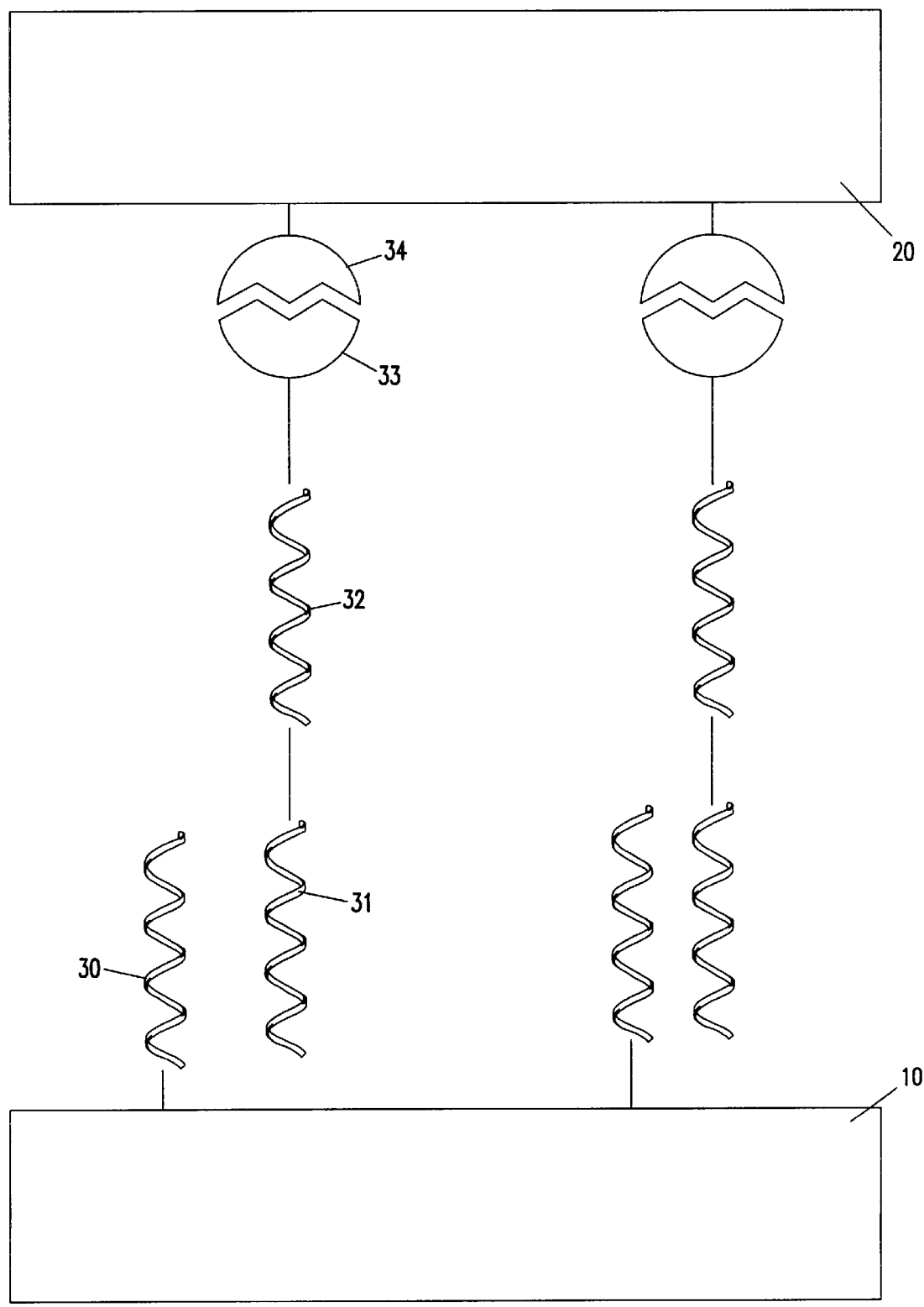
FIG. 1A shows one embodiment of the claimed system. The master array comprises a master array support 10 and attached address ligands 30 that are nucleic acid sequences. The address ligands are attached to the master array support. Each multi-ligand conjugate contains three ligands shown as 31, 32, and 33. The first binding ligand 31 is a nucleic acid sequence hybridized with a specific address ligand 30 of the master array. Each multi-ligand conjugate also contains a second binding ligand 32 that can is a nucleic acid sequence that can hybridize with a specific target nucleic acid sequence that may be present in a biological sample. In the system, the second binding ligand is not hybridized because there is no biological sample present. The system is a transitory structure formed in the process of making an assay array; the resulting assay array can be used to detect target nucleic acid sequences that may be present in a biological sample. Each multi-ligand conjugate contains a binding ligand 33 bound to a binding partner 34 that is attached to an assay array support 20.

Dissociation of the system shown in FIG. 1A results in the recovery of the master array as well as formation of an assay array. The system can be used to reproducibly produce assay arrays.

Figure 1B:
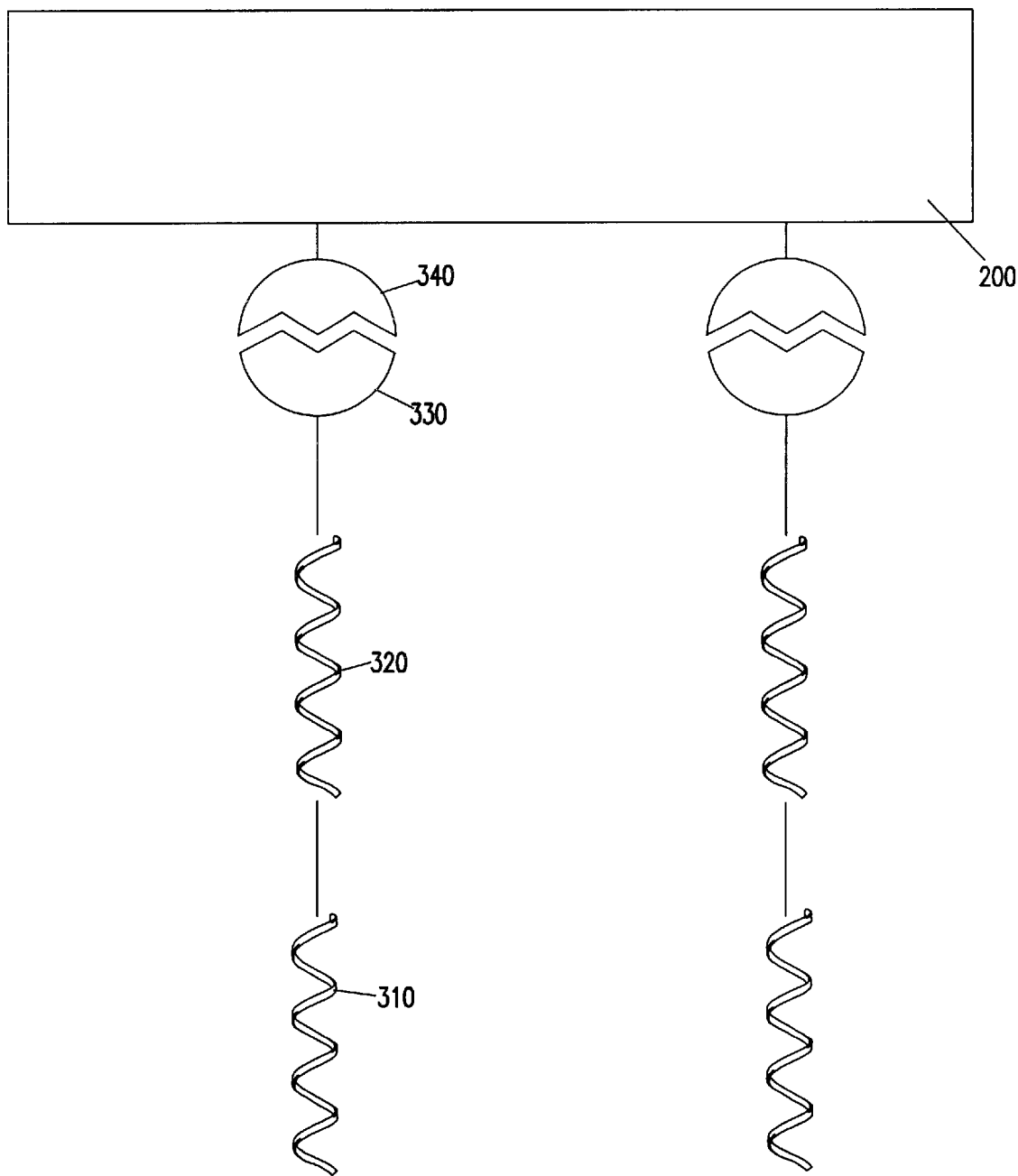

FIG. 1B shows the resulting assay array formed after dissociation of the system. Each multi-conjugate ligand comprises a first binding ligand 310, a second binding ligand 320, and a third binding ligand 330 that is attached to an assay support 200 through a binding partner 340 attached to the assay support 200. The second binding ligand but not the first binding ligand can bind in a complementary manner to a specific target nucleic acid sequence that may be present in a biological sample.

Figure 1C:
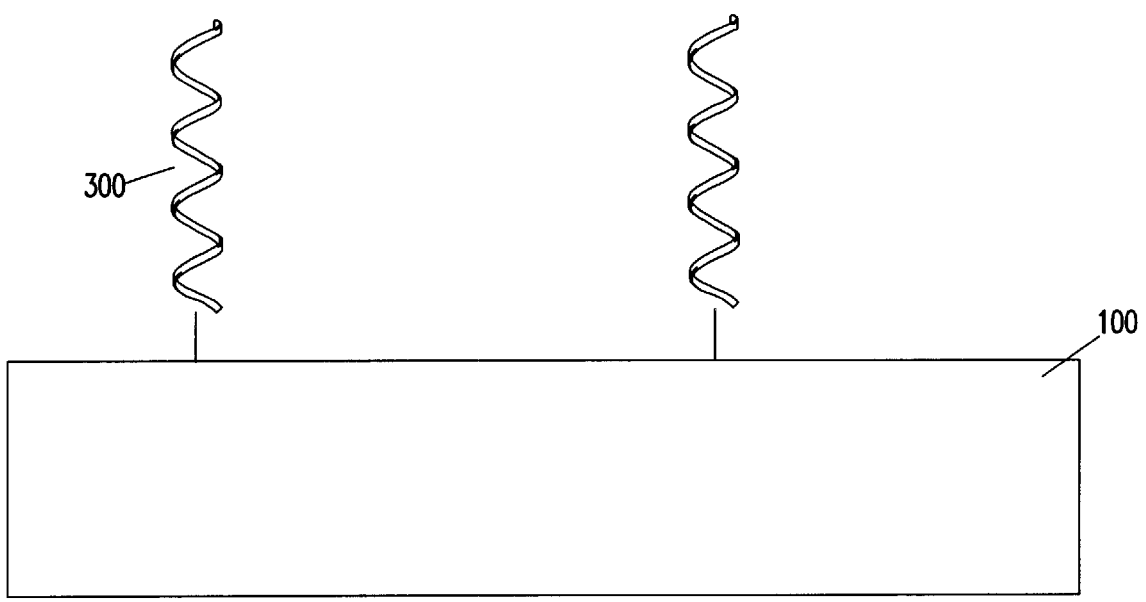

FIG. 1C shows the master array comprising a master array support 100 and attached address ligands 300. The master array can be reused to prepare additional assay arrays like those in FIG. 1B.

Figure 2A:
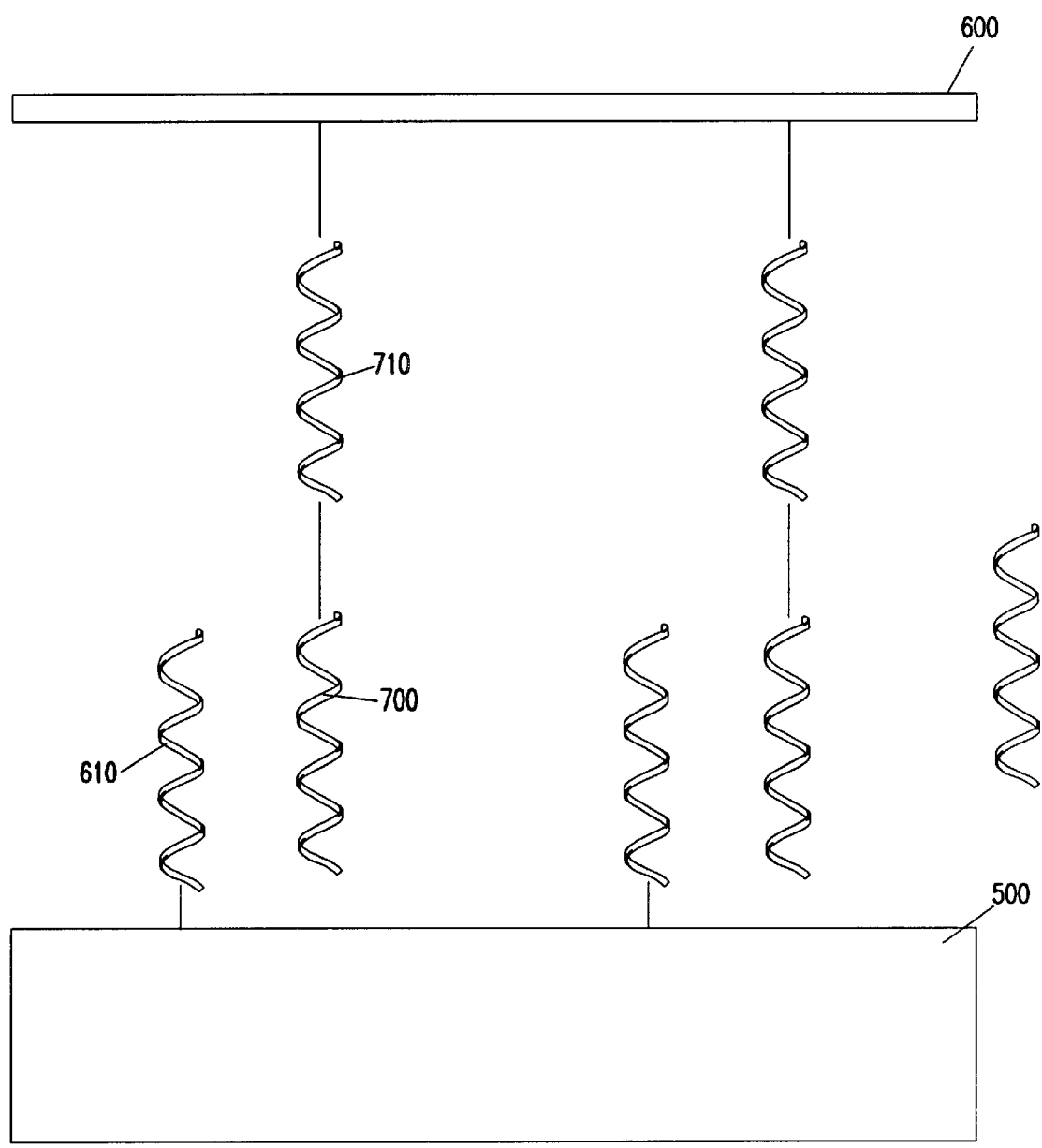

FIG. 2A shows another embodiment of the claimed system. The master array comprises a master array support 500 and attached address ligands 610 that are nucleic acid sequences. Each multi-ligand conjugate contains a first binding ligand 700 that is a nucleic acid sequence hybridized with a specific address ligand 610 of the master array. Each multi-ligand conjugate also contains a second binding ligand 710 that is a nucleic acid sequence that can hybridize with a specific target nucleic acid sequence that may be present in a biological sample. In the system, the second binding ligand is not hybridized because there is no biological sample present. The multi-ligand conjugate contains at least one polymerizable group (acrylic or vinyl group) that reacts to form a polymer film backing 600 while substantially maintaining the position of the multi-ligand conjugates.

DETAILED DESCRIPTION

The present invention provides a method and system for reproducibly preparing a specific binding ligand array, such as a nucleic acid array. As used herein, "nucleic acids" include polymeric molecules such as deoxyribonucleic acid (DNA), ribonucleic acid (RNA), peptide nucleic acid (PNA), or any sequence of what are commonly referred to as bases joined by a chemical backbone that have the ability to form base pairs or hybridize with a complementary chemical structure. The nucleic acid can be provided in any suitable form, e.g., isolated from natural sources, recombinantly produced, or artificially synthesized. The word "oligonucleotide," in turn, will be used interchangeably with the term "nucleic acid" to refer generally to short chain (e.g., less than about 100 nucleotides in length, and typically 20 to 50 nucleotides in length) nucleic acid sequences, e.g., as prepared using synthetic techniques presently available in the art, such as solid support nucleic acid synthesis. While the invention will be described with particular reference to nucleic acids (and their ability to specifically "bind" via hybridization), it is understood that the invention has applicability to other specific binding ligands as well, such as immunological binding pairs or other ligand/anti-ligand binding pairs.

In one embodiment, the present invention provides a master array having immobilized thereon a plurality of address oligonucleotides, the pattern of which can be controlled and/or determined by any suitable means. Thereafter, a composition comprising a plurality of multi-ligand conjugates is brought into binding proximity with the master array, under conditions suitable to permit a first (e.g., oligonucleotide) binding domain of the multi-ligand conjugate to bind (e.g., hybridize) with complementary address oligonucleotides on the master array support.

In a particularly preferred embodiment, the third ligand is provided in the form of a binding ligand (e.g., biotin). The master array and multi-ligand conjugate can be prepared and combined in substantially the manner described above, with the third binding ligand then serving to transfer the resultant conjugate complex to the assay array support. The master array containing bound conjugate molecules can be brought into binding proximity with an assay array support. The assay array support, in turn, bears attachment sites (e.g., binding partner molecules) adapted to bind (e.g., non-covalently) with the third binding ligand of the multi-ligand conjugate. The assay array support can be brought into binding proximity under conditions suitable to permit the binding partner molecules of the assay array support to bind to corresponding binding ligands on the multi-ligand conjugate, thus forming a transitory "sandwich" structure in the form of master array—multi-ligand conjugate—assay array support.

In an optional preferred embodiment, the multi-ligand conjugate of the present invention further comprises a polymerizable group (e.g., an acrylic or vinyl group). In this embodiment, once the address oligonucleotides of the master array have each hybridized with their respective first binding domains of the multi-ligand conjugates, the polymerizable group can be reacted, using reagents and conditions within the skill of those in the art, to allow the formation of a polymer film. The polymerizable groups are copolymerized into the film backing while substantially maintaining their respective positions. The film can be used as is, or optionally stabilized (e.g., gelled, laminated with another layer, or otherwise solidified) such that it is sufficiently stable (e.g., self supporting) to maintain the spatially-defined locations of each "address." Simultaneously or thereafter, this polymeric backing can be transferred to, or otherwise incorporated into, an assay array surface in a manner that maintains the desired orientation of conjugates.

Once the "sandwich" structure has been formed, the base pairing between address oligonucleotide (of the master array) and complementary oligonucleotides (of the conjugate) can then be disassociated, in order to permit the assay array to be removed with the multi-ligand conjugates attached thereto. The conjugates are attached in a spatial relationship that is sufficiently true to that established by their initial binding to the master array surface, thereby permitting the location of target nucleic acids to be maintained and determined. The master array, in turn, can be reused repeatedly and in a similar manner to provide additional, and substantially identical, assay arrays. In another aspect, the present invention provides a plurality of identical assay arrays, e.g., formed by replicating a common master array or sequentially replicating one or more assay arrays.

In yet another aspect, the present invention provides a method and system for directly preparing reusable nucleic acid arrays, without the need to first prepare or replicate a master array, e.g., wherein the assay array surface is provided in the form of an optical fiber array. In one such embodiment, each of the fibers is provided with a nucleic acid adapted to hybridize to its complementary nucleic acid in a detectable fashion. Suitable fiber arrays for use in such an embodiment are described, for instance, in (K. Michael et al.), Analytical Chem. 70(7):1242 (1998).

The assay arrays of this invention, in turn, are preferably adapted to detect a wide variety of nucleic acids in a biological sample. In the course of its use, an assay array can be exposed to a test solution suspected of containing one or more target nucleic acids (e.g., genes or gene fragments), under conditions suitable to permit the target nucleic acids to be bound through hybridization to their corresponding oligonucleotide binding domain complement on the assay array. The presence or absence of the target nucleic acid on the assay array can be determined with the chosen signal generation and detection system.

A system of the present invention provides a number of advantages over current methods, including, for instance, an optimal combination of such properties as nucleic acid probe density, ease of use, reproducibility, and reduced cost. The present invention can, for instance, provide a higher nucleic acid probe density than commercial approaches that currently rely on photolithography. Such probe density is achieved, for instance, by the use of micro-beads that are smaller than the wavelength of photolithography light systems. Further, the present invention can provide improved assay specificity, e.g., by the use of oligonucleotides that are longer (and therefore more specific as to binding) than those currently available through photolithographic synthesis.

Moreover, the present assay array can be used with conventional array readers to provide a variety of target nucleic acid capacities, depending, for instance, upon the area density of the immobilized array. The present system can also provide a significant reduction in the cost of manufacture of high-density array slides. The cost of preparing the master array can itself be reduced, for instance, through the use of patterned deposition and immobilization of address oligonucleotide sequences, optionally with the use of micro-beads.

In a preferred embodiment, the system employs the use of a dedicated master array comprising a plurality of different address oligonucleotides. The support surface of such an array can be fabricated from any suitable material to provide an optimal combination of such desired properties as stability, dimensions, shape, and surface smoothness. The address oligonucleotides can be attached to the support surface directly or via linkers to the surface (e.g., by providing and/or derivatizing either the surface, the oligonucleotide, or both, with mutually reactive groups). In a particularly preferred embodiment, the master array support surface is coated with a plurality of linking micro-beads that, in turn, have oligonucleotides attached thereto. Hence, when used in combination with linking micro-beads, the master array support surface is preferably provided with sufficient smoothness such that topographical irregularities are smaller than the radius of the linking micro-bead (e.g., a roughness no greater than 50% the diameter of the linking micro-beads of the master array).

A master array support surface of this sort is preferably provided in the form of a planar, non-porous solid support having at least a first surface. A plurality of different oligonucleotides can be attached to the first surface of the solid support at a density exceeding 100 different oligonucleotides/cm$^2$, and preferably exceeding 1000 different oligonucleotides/cm$^2$, wherein each of the different oligonucleotides is attached to the surface of the solid support in a different predefined region, has a different determinable sequence, and is at least 4 nucleotides in length, and preferably at least 10 nucleotides, and more preferably 30 nucleotides in length. The oligonucleotides are provided in sufficient length to provide suitable diversity of "addresses" on the master array, while at the same time avoiding substantial complementarity to target nucleic acid (e.g., naturally-occurring) sequences to be detected by the assay array.

In a preferred embodiment, the master array includes at least 1,000, and more preferably at least 10,000, different address oligonucleotides attached to the first surface of the solid support, each located (e.g., spotted) in a predefined region physically separated from other regions. Given the preference for multiple sites of each oligonucleotide, the total number of oligonucleotide sites in a single array can often exceed 10,000.

The master array can be fabricated from any suitable material, including, for example, biological or nonbiological, organic or inorganic materials. For example, the master array can be fabricated from any suitable plastic or polymer, silicon, glass, ceramic, or metal, and can be provided in the form of a solid, resin, gel, rigid film, or flexible membrane. Suitable polymers include polystyrene, poly(alkyl)methacrylate, poly(vinylbenzophenone), and polycarbonate. Preferred materials include glass and silicon. In a particularly preferred embodiment, the master array is provided with planar dimensions of between about one-half cm and about 7.5 cm in length, and between about one-half cm and 7.5 cm, and preferably between about 1 and 2 cm, in width. Arrays can also be singly or multiply positioned on other supports, such as microscope slides (e.g., having dimensions of about 7.5 cm by 2.5 cm).

The support surface of the master array can also be prepared by uniformly distributing photoreactive bi- or poly-functional reagents on the surface and thereafter coupling these reagents to the surface. In one embodiment, for example, a silicon chip with sufficient smoothness is cleaned and reacted with a photoreactive organosiloxane reagent. This reagent can be prepared, for instance, by bonding a commercial organosiloxane reagent (such as aminopropyldimethylmethoxy siloxane) with a thermochemically reactive photoreagent such as the acid chloride of benzoylbenzoic acid. The resulting photoreactive siloxane reagent can then be reacted with the silicon oxide surface of the master array support to provide a smooth surface, primed with photoactivatible groups. The photoreactive groups on the resulting primed surface can be activated and used to coat the oligonucleotides, directly or indirectly by means of linkers, onto the surface.

In an alternative embodiment, a melt or concentrated solution of a reagent having both latent reactive (e.g., photoreactive) groups and ligand-attractive (e.g., charged, cationic) groups can be used. For instance, a polystyrene derivative containing one or more of both types of groups (e.g., thiocholine derivatives of polyvinylbenzoic acid) can be deposited on the surface of the master array to provide a reactive surface film for immobilization of the address oligonucleotides. The surface of the master array can be illuminated to generate a smooth photoreactive surface. Optionally, the ligand-attractive group (e.g., cation/thiocholine) is removed, if desired.

As used herein, the term "address oligonucleotides" will be used to refer to nucleic acid sequences that are selected to be non-complementary with target nucleic acid sequences present in a biological sample to be tested. As a result, the address oligonucleotides, are expected to not form base pairs or otherwise hybridize with any target nucleic acids found in a particular biological test sample, thereby avoiding or minimizing the possibility of background or false positive readings. Preferably, these address oligonucleotides are between 10 and 100 nucleotides in length, and most preferably between 20 and 50 nucleotides in length.

Deposition of the address oligonucleotides onto the master array surface can be accomplished in any suitable manner, including for instance, by direct attachment or indirect attachment through a linker (e.g., a linking micro-bead). For example, if the address oligonucleotide is bound to a micro-bead, which is in turn to be bound to the master array, deposition can be accomplished by a gravity-based method in which the specific gravity of the micro-bead causes the individual micro-bead carrying the address oligonucleotide to contact the master array surface. This deposition forms an ordered but random pattern on the master array surface. The resultant surface can then be illuminated under conditions suitable to activate the photoreactive groups and cause bond formation between the micro-bead carrying address oligonucleotide and the master array support surface.

In a particularly preferred embodiment, oligonucleotides are immobilized onto the master array surface using photoactivatable compounds to form bonds between the address oligonucleotide and the master array support surface. These photoactivatable compounds can be provided in any suitable manner, e.g., by the master array support surface or the address oligonucleotides themselves. In one embodiment, for instance, the master array support surface is coated with a photoreactive (e.g., photosiloxane) reagent in order to provide a latent reactive surface for the formation of bonds with the address oligonucleotides. Thereafter, a solution containing a plurality of address oligonucleotides can be applied to the master array support surface. The master array is illuminated with long-wavelength ultraviolet or visible light to photochemically fix the address oligonucleotides onto the master array support surface. In an alternative embodiment, the address oligonucleotides themselves are photoreactive.

Preferably, address oligonucleotides of the present invention include one or more pendent latent reactive (preferably photoreactive) groups covalently attached, directly or indirectly, thereto. Photoreactive groups are defined herein, and preferred groups are sufficiently stable to be stored under conditions in which they retain such properties. See, e.g., U.S. Pat. No. 5,002,582, the disclosure of which is incorporated herein by reference. Latent reactive groups can be chosen that are responsive to various portions of the electromagnetic spectrum, with those responsive to ultraviolet and visible portions of the spectrum (referred to herein as "photoreactive") being particularly preferred.

Photoreactive groups respond to specific applied external stimuli to undergo active specie generation with resultant covalent bonding to an adjacent chemical structure, e.g., as provided by the same or a different molecule. Photoreactive groups are those groups of atoms in a molecule that retain their covalent bonds unchanged under conditions of storage but that, upon activation by an external energy source, form covalent bonds with other molecules.

The photoreactive groups generate active species such as free radicals and particularly nitrenes, carbenes, and excited states of ketones upon absorption of electromagnetic energy. Photoreactive groups may be chosen to be responsive to various portions of the electromagnetic spectrum, and photoreactive groups that are responsive to e.g., ultraviolet and visible portions of the spectrum are preferred and may be referred to herein occasionally as "photochemical group" or "photogroup".

Photoreactive aryl ketones are preferred, such as acetophenone, benzophenone, anthraquinone, anthrone, and anthrone-like heterocycles (i.e., heterocyclic analogs of anthrone such as those having N, O, or S in the 10-position), or their substituted (e.g., ring substituted) derivatives. Examples of preferred aryl ketones include heterocyclic derivatives of anthrone, including acridone, xanthone, and thioxanthone, and their ring substituted derivatives. Particularly preferred are thioxanthone, and its derivatives, having excitation energies greater than about 360 nm.

The functional groups of such ketones are preferred since they are readily capable of undergoing the activation/inactivation/reactivation cycle described herein. Benzophenone is a particularly preferred photoreactive moiety, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbonhydrogen) is not available for bonding, the ultraviolet light-induced excitation of the benzophenone group is reversible and the molecule returns to ground state energy level upon removal of the energy source. Photoactivatible aryl ketones such as benzophenone and acetophenone are of particular importance inasmuch as these groups are subject to multiple reactivation in water and hence provide increased coating efficiency.

The azides constitute a preferred class of photoreactive groups and include arylazides ($C_6R_5N_3$) such as phenyl azide and particularly 4-fluoro-3-nitrophenyl azide, acyl azides (—CO—$N_3$) such as benzoyl azide and p-methylbenzoyl azide, azido formates (—O—CO—$N_3$) such as ethyl azidoformate, phenyl azidoformate, sulfonyl azides (—$SO_2$—$N_3$) such as benzenesulfonyl azide, and phosphoryl azides $(RO)_2PON_3$ such as diphenyl phosphoryl azide and diethyl phosphoryl azide. Diazo compounds constitute another class of photoreactive groups and include diazoalkanes (—$CHN_2$) such as diazomethane and diphenyldiazomethane, diazoketones (—CO—$CHN_2$) such as diazoacetophenone and 1-trifluoromethyl-1-diazo-2-pentanone, diazoacetates (—O—CO—$CHN_2$) such as t-butyl diazoacetate and phenyl diazoacetate, and beta-keto-alpha-diazoacetates (—CO—$CN_2$—CO—O—) such as t-butyl alpha diazoacetoacetate. Other photoreactive groups include the diazirines (—$CHN_2$) such as 3-trifluoromethyl-3-phenyldiazirine, and ketenes (—CH═C═O) such as ketene and diphenylketene.

Upon activation of the photoreactive groups, the reagent molecules are covalently bound to each other and/or to the material surface by covalent bonds through residues of the photoreactive groups. Exemplary photoreactive groups are shown as follows.

| Photoreactive | Group |
|---|---|
| aryl azides | amine |
| acyl azides | amide |
| azidoformates | carbamate |
| sulfonyl azides | sulfonamide |
| phosphoryl azides | phosphoramide |
| diazoalkanes | new C—C bond |
| diazoketones | new C—C bond and ketone |
| diazoacetates | new C—C bond and ester |
| beta-keto-alpha-diazoacetates | new C—C bond and beta-ketoester |
| aliphatic azo | new C—C bond |
| diazirines | new C—C bond |
| ketenes | new C—C bond |
| photoactivated ketones | new C—C bond and alcohol |

The photoactivatable nucleic acids of the invention can be applied to any surface having carbon-hydrogen bonds, with which the photoreactive groups can react to immobilize the nucleic acids to surfaces. Examples of appropriate substrates include, but are not limited to, polypropylene, polystyrene, poly(vinyl chloride), polycarbonate, poly(methyl methacrylate), parylene and any of the numerous organosilanes used to pretreat glass or other inorganic surfaces. The photoactivatable nucleic acids can be printed onto surfaces in arrays, then photoactivated by uniform illumination to immobilize them to the surface in specific patterns. They can also be sequentially applied uniformly to the surface, then photoactivated by illumination through a series of masks to immobilize specific sequences in specific regions. Thus, multiple sequential applications of specific photoderivatized nucleic acids with multiple illuminations through different masks and careful washing to remove uncoupled photonucleic acids after each photocoupling step can be used to prepare arrays of immobilized nucleic acids. The photoactivatable nucleic acids can also be uniformly immobilized onto surfaces by application and photoimmobilization.

Immobilization of the address oligonucleotide onto the master array support surface can also be accomplished, for example, by placing address oligonucleotide-loaded microbeads at specific addresses on a photoreactive surface. The micro-beads can be placed, for instance, by such techniques as electrostatic attraction, electrode or magnetic probes, or optical tweezers.

More preferably, the linking micro-beads containing address oligonucleotides are immobilized in a spaced relationship onto the master array support surface. In such an embodiment, a woven screen having spaces only slightly larger than the bead diameter can be used as, or positioned upon, the surface of the master array, in order to promote deposition of micro-beads onto the surface in a separated, but ordered, configuration.

Other suitable methods for immobilization of the address oligonucleotide include chemical modification of the oligonucleotide (e.g., thiol modification), and non-covalent attachment by high-affinity binding agent (e.g., avidin-biotin). The surface of the master array support, in turn, can be derivatized (e.g., by amine groups) in order to link a corresponding reactive group provided by the oligonucleotide itself or a suitable cross-linking reagent. Alternatively, a binding partner (e.g., streptavidin) can be directly attached to the master array support surface, allowing interaction between the address oligonucleotide and the support surface of the master array. Other methods include adsorption of unmodified or modified oligonucleotides, as well as immobilization of the oligonucleotides onto the support surface by ink jet or "needle" printing with thermochemical immobilization of soluble probes on an activated master array support surface.

The typical master array of the present invention includes a large number of address oligonucleotides immobilized onto its surface, each in a discrete location or address. The word "address," as used in this sense, refers to a spatially-defined location upon the support surface that is sufficiently distinct to permit an oligonucleotide bound thereto to be identified and distinguished. The result of this immobilized crystalline array provides a master array containing a large number of unique "addresses" on its surface.

In a particularly preferred embodiment of the invention, the master array support surface contains redundant address oligonucleotides immobilized thereon, such that a particular address appears at a plurality of spatially-defined locations on the master array. As a result of this redundancy, a particular multi-ligand conjugate containing the complementary sequence to a specific address oligonucleotide will be able to bind at any of a plurality of locations on the master array. This redundancy of any particular address on the master array serves to increase the sensitivity of the assay for detection of corresponding target nucleic acid within a sample. For example, in one embodiment, the master array will contain an address sequence that is immobilized to the support surface at between 1 and 100, preferably between 2 and 10, different locations. In such a preferred embodiment therefore, detection of the target nucleic acid associated with the redundant address will take place at a number of different locations on the master array.

In one embodiment described above, the address oligonueleotides can be provided in immobilized form, e.g., in the form of individual linking micro-beads, each bearing a plurality of identical "address" oligonueleotide sequences. In one such embodiment, an organized array of linking micro-beads loaded with address oligonucleotides can be deposited on a smooth master array support surface primed with photoreactive groups.

The linking micro-beads can be procured from commercial sources and loaded with oligonucleotides by the use of commercially available processes and materials. Preferably, the linking micro-beads are selected to have a specific gravity sufficient to allow them to settle onto the surface of the master array by gravity (while avoiding the effects of Brownian motion). The attachment of the address oligonucleotides to the linking micro-bead is preferably accomplished by the formation of covalent bonds between the oligonucleotide and the bead. In one particularly preferred embodiment, the surface of the linking micro-bead is reacted with an organosiloxane reagent containing a thermochemically reactive group (e.g., an epoxy).

Glycidoxypropyltriethoxy siloxane, for instance, can be reacted with the micro-beads to provide an epoxy surface. The 5' terminus of the address oligonucleotide is, in turn, modified to produce a terminus containing alkylamine groups on spacers. The epoxy siloxane of the micro-bead surface reacts with the alkyl amine positioned at the terminus of the address oligonucleotide, forming a bond between the address oligonucleotide and the micro-bead surface.

An array of micro-beads can be deposited from an aqueous suspension, optionally containing block copolymers having both photoreactive groups and ligand-attractive groups (e.g., ionic groups such as quaternary amines) thereon. Monodisperse micro-beads (e.g., between about one-half micron and 5 microns in diameter), previously loaded with address oligonucleotides, are applied to the master array support surface from suspension in an aqueous solution of the copolymers. The cationic reactive group serves to associate with the oligonucleotide sequences on the beads, while the aromatic block (e.g., oligostyrene) serves to associate with and couple to the photoreactive surface. In a particularly preferred embodiment, the linking micro-beads are provided in slight excess.

The smooth flat photoreactive master array support surface is exposed to a slurry of linking micro-beads with address oligonucleotide sequences immobilized thereon, in sufficient number to provide at least a monolayer of linking micro-beads on the master array support surface. This slurry is comprised of approximately equal numbers of beads with each of the desired address oligonucleotide sequences, plus a multiple (e.g., at least 3-fold) of beads containing no oligonucleotides. The number of oligonucleotide-coated beads is sufficient to provide a small redundancy (e.g., at least 3-fold) of each target nucleic acid-specific site.

The master array is incubated in the solution containing linking micro-beads in the dark or dim light, so as to avoid premature activation of the photogroups. As the solvent (preferably aqueous) evaporates from the slurry pool on the photoreactive surface, the uniform-sized beads are packed into a two-dimensional "crystalline" arrangement, optionally being spaced apart and positioned, e.g., using a micro-screen as described herein.

This ordered arrangement can then be "fixed" in place, e.g., by illumination in the dry state to form carbon-carbon bonds between the photoreactive groups on the master array support surface and the organic groups (mostly oligonucleotides) on the linking micro-beads. A patterned array of beads, having settled by gravity onto the photoreactive surface, can be photochemically fixed to the surface by illumination with long-wave ultraviolet or visible light. This illumination activates the photoreactive organosiloxane reagent, which in turn, forms bonds with the address oligonucleotides. Optionally, once the arrayed linking micro-beads have been photocoupled to the master array support surface, the unbound block copolymer can be rinsed from the master array. This rinsing removes subsequent interference (e.g., during hybridization steps) with the oligonucleotide sequences on the outer side of the beads.

The spatially-defined location of each immobilized address oligonucleotide can then be determined using any suitable means, e.g., by fluorescent hybridization involving the sequential addition of fluorescent-labeled, complementary sequences to the array, followed by rinsing and scanning between each addition. Fluorescent-labeled oligonucleotides complementary to each of the address oligonucleotide sequences are available or can be synthesized to contain one of several (e.g., ten or more) different fluorescent compounds commonly known to be distinguishable from each other. A plurality (e.g., ten) different oligonucleotides can be prepared, each having a different, known sequence complementary to an address sequence on the surface and each having a corresponding distinguishable fluorophore. The labeled probes can be simultaneously applied to the surface and hybridized, e.g., at 55° C. for 30 minutes. The surface is then rinsed and scanned to identify the locations of each of the ten sequences. Another set of ten sequences is then hybridized to the surface and scanned to identify the second set of ten sequences. This process is continued until all of the addresses are identified, after which the master array is stripped of hybridized oligonucleotides, e.g., by immersing in boiling water for two minutes, and used for preparing replicate assay arrays.

A preferred system of the present invention further includes a multi-ligand conjugate containing a plurality of active (e.g., binding or polymerizable) domains. In accordance with the invention, the individual ligands can be attached to a core atom or molecule in any suitable manner and/or order, e.g., individually or together (e.g., in linear sequence and at a single location or at a plurality of locations). For example, in one embodiment, the ligands are attached to the core simultaneously, e.g., under similar reaction conditions. Optionally, the ligand serving as the third ligand is attached to the core after hybridization between the address oligonucleotide of the master array and the complementary oligonucleotide provided by the multi-ligand conjugate. In this embodiment, the third ligand is present as a separate reagent; however, attachment of the third ligand is capable of taking place under the same or similar reaction conditions as the first and second binding domains. In yet another embodiment, each of the ligands is attached to the transfer core under separate conditions of separate reactions.

The sequence of attachment of these ligands to the core of the multi-ligand conjugate is not crucial to the present invention, and so long as the individual active (e.g., binding) domains are available for binding their specific complement, they can be attached to the core or to one another in any order. In a particularly preferred embodiment, each individual binding domain is attached to the core individually, at a plurality of locations on the surface.

Optionally, the core of the multi-ligand conjugate is itself provided in the form of a transfer micro-bead. The micro-beads useful in preparing a multi-ligand conjugate can be of the same variety as those described above with respect to the "linking micro-beads." Preferred beads are desirably spherical, homogeneous in size, with a specific gravity greater than that of water. Also, preferred beads have a chemical composition, or at least surface, that is subject to bonding with organic reagents. For example, homogeneous silica spheres of between about 0.5 micron and about 5 microns ($\mu$) diameter can be reacted with an organosiloxane reagent containing a thermochemically reactive group (e.g., epoxy), in order to couple the reagent to corresponding groups of a binding ligand.

In one such embodiment, for instance, glycidoxypropyl-triethoxy siloxane is reacted with glass micro-beads under published reaction conditions, to provide epoxy-glass surfaces. The three binding domains of the present invention, each terminated with alkylamine groups on spacers, can be readily coupled with the epoxy groups on the surface of the bead.

First and second oligonucleotide binding domains can be attached to the transfer microbead in any suitable fashion, e.g., alkylamine-terminated binding domains can be synthesized and thermochemically attached. For the first and second oligonucleotide binding domains, the lengths of the oligonucleotides are optimized for desired hybridization strength and kinetics (usually in the 20–50 nucleotide range). The first binding domain comprises an oligonucleotide that is complementary to the address oligonucleotide immobilized onto the master array support surface, while the second binding domain is complementary to a chosen target nucleic acid suspected or known to be in a sample to be tested. Preferably, the sequences of the first binding domain are not complementary either to one another or to any known natural gene sequence and/or gene fragment with significant probability of being present in the biological sample. As a result, the first binding domain oligonucleotide sequences will hybridize only with their respective complementary address oligonucleotide sequences immobilized onto the master array support surface. This avoids cross-reactivity (e.g., cross-hybridization) between the first binding domain, which is responsible for placing the multi-ligand conjugate at a spatially-defined location on the assay array support surface, and the target nucleic acid sequences screened in the test sample.

Oligonucleotides are selected for the first binding domain by preparing the complementary sequence to the random sequences comprising the address oligonucleotides of the master array. This preparation can be accomplished using any suitable methods known in the art, for example, by solid phase DNA synthesis. Once the oligonucleotides for the first binding domain have been synthesized, a terminus of each oligonucleotide can be modified to contain an alkylamine group on a spacer.

Oligonucleotides are selected for the second binding domain by first selecting the target nucleic acids (e.g., genes and/or gene fragments) to be detected by the microarray to be fabricated in accordance with the invention. The sequences of these genes and/or gene fragments may be known, or may be determined using techniques well known in the art (e.g., Sanger dideoxy method, PCR sequencing, etc.). Once the second binding domains have been chosen, a terminus of each oligonucleotide can be modified to contain an alkylamine group on a spacer.

The third ligand (e.g., binding domain or polymerizable group) can be of any suitable type, and can be attached to the core or transfer micro-bead in any suitable fashion. In a preferred embodiment, for instance, the third ligand is a binding ligand provided in the form of a biotin-poly (alkyleneoxide) amine derivative. Such a derivative can be prepared, for instance, by reacting an N-oxysuccinimide ester of biotin with a poly(ethyleneoxide) diamine of approximately the same molecular length as the oligonucleotide derivatives to be placed on the same core or micro-bead.

The multi-ligand conjugates can be fabricated to include oligonucleotides that are complementary to, and thus will hybridize with, any desired target nucleic acid found in a biological sample, and which has a known, or determinable, sequence. In one embodiment, the various second binding domains of the multi-ligand conjugates of the present invention can comprise a wide array of oligonucleotides that are complementary to various target nucleic acids found in a biological sample.

In an alternative embodiment, the second binding domains of the multi-ligand conjugates will be fabricated such that the resulting assay array will locate target nucleic acids of a particular family of naturally-occurring genes. One example of this particular embodiment would be a set of multi-ligand conjugates containing second binding domains complementary to the 50–60 known target sequences of cystic fibrosis. Thus, the resulting assay array would be fabricated such that it detects the presence of the sequences known to be associated with this disorder only.

The third ligand of the multi-ligand conjugate of the present invention optionally comprises a binding ligand adapted to form bonds with a corresponding binding partner. The third ligand can be attached directly to the core or transfer micro-bead of the multi-ligand conjugate, or indirectly by the use of a spacer, in a manner that allows the ligand to be free of steric hindrance (e.g., steric hindrance caused by proximity of the ligand to the transfer micro-bead). In other words, use of a spacer to attach the third ligand will ensure that the ligand is sufficiently distant from the core or surface of the transfer micro-bead to allow it to perform its desired function, e.g., polymerize or bind with a corresponding binding partner contained on the assay array surface. In a particularly preferred embodiment, the third ligand is attached to the core or transfer micro-bead via a hydrophilic spacer, e.g., a polyethylene glycol spacer, of sufficient length to allow the binding domain to be free of steric hindrance.

In an alternative embodiment, the third ligand is provided in solution, rather than attached to the micro-bead or core of the multi-ligand conjugate. In this embodiment, the third ligand is incorporated after hybridization of the master array address oligonucleotide with its complementary first binding domain of the multi-ligand conjugate. Therefore, in this embodiment, the third ligand is incorporated into the complex formed on the master array after attachment of the multi-ligand conjugate, and before the assay array is brought into binding proximity to the master array. Preferably, the addition of the third ligand does not require different reaction conditions from that of the first and second binding domains; rather, the addition of the third ligand can take place under the same conditions.

In a preferred embodiment, the third ligand is attached to the multi-ligand conjugate using photoreactive chemistry. In this embodiment, the surface of a micro-bead is pretreated, for example, with an organosiloxane in order to prepare the surface for reacting with photoreactive compounds. In this embodiment, the third ligand is attached to a hydrophilic spacer, which is, in turn, attached to a photoreactive group. The photoreactive group allows bond formation between the spacer (attached to the binding ligand) and the transfer micro-bead.

In an alternative embodiment, wherein the invention includes the use of porous linking micro-beads immobilized onto the surface of the master array, such micro-beads having attached thereto address oligonucleotides, the transfer micro-bead of the multi-ligand conjugate is not required. In this embodiment, the porous linking micro-beads can be immobilized onto the surface of the master array, each porous micro-bead having a plurality of address oligonucleotides attached to its surface. In this embodiment, the multi-ligand conjugates comprise a first binding domain complementary to the address oligonucleotide, a second binding domain complementary to a target nucleic acid sequence found in a biological sample, and a third ligand comprising a binding ligand. The multi-ligand conjugate does not contain a transfer micro-bead, but rather a chemical (e.g., atomic or molecular) core.

A plurality of multi-ligand conjugates are applied to the master array and incubated under conditions suitable to allow hybridization of the address sequence of the master array with its complementary oligonucleotide contained within the multi-ligand conjugate. Those skilled in the art will be able to determine suitable conditions of temperature, salt concentration, and buffer composition. For a discussion of hybridization conditions and methods for applying them, see *Nucleic Acid Hyrbridization: A Practical Approach*, Hames and Higgins, eds., 1985, the disclosure of which is incorporated herein by reference.

The third ligand of the multi-ligand conjugate can be provided in the form of a polymerizable group, e.g., to allow the conjugates to form into a stable film while in position on the master array. Suitable polymerizable groups include, for example, acrylic and vinyl groups. In a preferred embodiment, the polymerizable groups are adapted to undergo addition polymerization, in the presence of added monomers and other reagents (e.g., initiators), to form a stable film. Polymerization can take place via any suitable reaction, including aqueous free-radical solution polymerization, exposure to heat, high energy radiation, ultrasonic waves, ultraviolet radiation, and ionic polymerization catalysts to produce water-soluble or swellable polymers. Further, polymerization of the groups can take place via base-catalyzed hydrogen-transfer polymerization. Those skilled in the art, given the present description, will appreciate the manner in which such groups can be used to copolymerize the ligands with other monomers, and in turn their corresponding conjugates, into the form of an integral polymeric structure, e.g., a film backing, which can in turn be used as or transferred to an assay array support surface.

The assay array support of the present invention can be fabricated from any suitable material to provide an optimal combination of such properties as stability of dimension, shape, and smoothness. Suitable materials for use in fabricating the assay array include those described as being useful for the master array itself, and preferably include silicon and glass. In a particularly preferred embodiment, the assay support is provided with dimensions measuring 50 square $\mu$m. Preferably, the assay array support is of comparable dimensions to the master array, in order to provide direct spatial relationships.

The surface of a discrete assay array support can be pretreated to facilitate attachment of the oriented conjugate layer. In a preferred embodiment, the assay array is provided in the form of a silicon chip that has been cleaned, polished and treated to provide a smooth silicon oxide surface. The silicon oxide surface can then be treated with an organosiloxane reagent (as described herein) to provide a smooth photoactivatable surface.

In one embodiment, the assay array support of the present invention can be coated with binding partner molecules adapted to form bonds with the third ligand of the multi-ligand conjugate. The assay array support surface can be prepared by coating the surface with a photoactivatable compound (e.g., photoreactive siloxane reagent) to render the surface photoreactive. Thereafter, the assay array support surface can be exposed to a solution containing binding partner molecules (e.g., avidin), and the solution illuminated, in order to allow bond formation between the binding partner and surface of the assay array. Optionally, the surface of the assay array is passivated prior to and/or after exposure to the binding partner, e.g., with a surfactant (e.g., a biotin triblock copolymer), to prevent non-specific binding of molecules found in the test sample to the assay array support surface.

In a particularly preferred embodiment, the binding partner is provided in the form of a monolayer upon the assay array support surface. Optionally, the binding partner can be provided in the form of a three-dimensional layer, e.g., an avidin-hydrogel composite of up to a micron thickness. Such a structure can be obtained, for instance, by loading the photoreactive assay array surface with a solution of avidin plus photoreactive hydrogel (e.g., copolymer of benzoyl-benzamidopropyl methacrylamide with vinylpyrollidone or acrylamide) and illuminating while wet.

In another particularly preferred embodiment, a thin film of photopolymer is applied to a dimensionally stable assay array support surface. A self-assembling monolayer film of passivating surfactant containing a high surface density (e.g., 0.1 pmol/mm$^2$) of high-affinity ligand group (e.g., biotin) is applied to the photoreactive surface. The monolayer surfactant film is then photocoupled to the surface, and any unbound surfactant is rinsed away. The passivated, ligand-loaded surface is saturated with high-affinity binding partner molecule (e.g., X-avidin), and any excess binding partner is rinsed away. Suitable high-affinity binding partner molecules include, for example, x-avidin film, or high-affinity antibody (e.g., anti-digoxygenin).

Optionally, the system further includes other components as well, including for instance, means (e.g., reagents) for use in disassociating complementary, hybridized oligonucleotides (e.g., the address oligonucleotide of the master array and its complementary oligonucleotide carried by the multi-ligand conjugate). For example, suitable means for disassociating the hybridized DNA include altering the temperature, pH, or salt concentration of the system.

Optionally, the system further comprises a scanner, as commercially available (e.g., a confocal fluorescence microscope as available from Molecular Dynamics) to detect the hybridization of nucleic acid targets to specific addresses.

In another aspect, the present invention provides a method for reproducibly preparing a nucleic acid array, the method comprising:

a) providing a master array having a support surface;
b) immobilizing (e.g., depositing and fixing, e.g., directly or via respective linkers or "linking" micro-beads) a plurality of address oligonucleotides on the master array support surface in the form of a patterned and optionally random array;
c) determining and recording the pattern of the immobilized address oligonucleotides (e.g., using fluorophore-coupled oligonucleotides for hybridization to the address oligonucleotide);
d) providing a plurality of free (i.e., nonimmobilized) multi-ligand conjugates, each multi-ligand conjugate comprising a core having (preferably independently) attached thereto: (i) at least one molecule of a first oligonucleotide binding domain, comprising an oligonucleotide sequence selected to be complementary to a particular address oligonucleotide sequence of the master array, (ii) at least one molecule of a second oligonucleotide binding domain, comprising an oligonucleotide sequence selected to be complementary to a characteristic oligonucleotide sequence of a target nucleic acid sequence (e.g., a gene and/or gene fragment), and (iii) at least one molecule of a third (and preferably non-oligonucleotide) ligand, selected from the group consisting of binding ligands and polymerizable groups (e.g., acrylic or vinyl groups);
e) contacting and incubating the multi-ligand conjugates with the master array support surface under conditions suitable to allow each address oligonucleotide to hybridize with its complementary first oligonucleotide binding domain of the multi-ligand conjugates (and optionally removing non-hybridized multi-ligand conjugates);
f) providing an assay array support surface,
g) contacting the hybridized multi-ligand conjugates with the assay support surface under conditions suitable to permit the conjugates to be transferred to the assay support in a pattern corresponding to their pattern on the master array, e.g., either by polymerizing a third ligand (provided in the form of a polymerizable group), or by binding a third ligand (provided in the form of a third binding ligand) with a corresponding attachment site provided by the assay support surface; and
h) disassociating the first binding domain from the master array support in a manner that permits the conjugates to remain upon the assay support surface in the desired pattern.

In use, the core (e.g., transfer micro-beads) bearing three or more ligands can be mixed in equal numbers and suspended in aqueous buffer. This suspension can contain an excess (over the hybridization capacity of the micro-beads on the master array) of each transfer micro-bead carrying the oligonucleotide sequence complementary to a characteristic oligonucleotide sequence of a target nucleic acid expected to be detected in a sample.

The master array surface can be flooded with this suspension of the chosen mixture of multi-ligand conjugates and solid-state hybridization can be allowed to proceed to near equilibrium. The excess multi-ligand conjugates can then be recovered from the hybridized master array by rinsing, and the bound conjugates either copolymerized to form a stable backing or bound to corresponding binding partners on the assay array. The master array is then available for a repeat replication process.

The master array can be used repeatedly to prepare corresponding assay arrays, which in turn can be packaged, stored and transported, e.g., in the wet or dry state. Upon removal from its package, an assay array will be ready to use in a routine hybridization assay protocol with a scanner. Moreover, the present invention provides a master array that is versatile in use—the master array can be used and reused, to create identical arrays or to change the function of the array (e.g., to alter the oligonucleotide sequence complementary to a characteristic oligonucleotide sequence of a target nucleic acid, such that the user can alter the target nucleic acid to be detected in a sample).

Those skilled in the art, given the present description, will appreciate the manner in which commercially available microarrays can themselves be used as master arrays of the present invention, to be replicated one or more times to form corresponding assay arrays. In this case, the individual nucleic acids of the commercial array, regardless of their original specificity, can each be considered as mere address sequences, and used in the manner described herein to provide assay arrays of any desired specificity.

In yet a further aspect, and particularly where the third ligand is provided in the form of a third binding ligand, the present invention provides a sandwich array comprising:

a) a master array comprising a support surface having a plurality of address oligonucleotide sequences immobilized thereon (e.g., directly or via respective linkers or "linking" micro-beads), the oligonucleotide sequences being immobilized in the form of a patterned, and optionally random array;

b) a plurality of multi-ligand conjugates, each multi-ligand conjugate comprising a core having (preferably independently) attached thereto: (i) molecules of a first oligonucleotide binding domain, each molecule comprising an oligonucleotide sequence complementary to a particular address oligonucleotide sequence of the master array, (ii) molecules of a second oligonucleotide binding domain, each molecule comprising an oligonucleotide sequence complementary to a characteristic oligonucleotide sequence of a target nucleic acid (e.g., a gene and/or gene fragment), and (iii) at least one molecule of a third (and preferably nonoligonucleotide) binding ligand selected from the group consisting of binding ligands and polymerizable groups (e.g., acrylic or vinyl groups), wherein the first oligonucleotide binding domain is hybridized to the corresponding address oligonucleotide immobilized onto the master array; and c) an assay array support comprising a support surface coated with attachment sites for the third binding ligand (such as, immobilized molecules of a corresponding binding partner specific for the third binding ligand), wherein the attachment site of the assay array is bound to the corresponding binding ligand of the multi-ligand conjugates.

Optionally, the sandwich array further comprises a linking micro-bead immobilized onto the surface of the master array, the linking micro-bead having attached thereto a plurality of address oligonucleotides.

In yet another alternative embodiment, the present invention provides a corresponding kit comprising one or more components for reproducibly preparing a nucleic acid array, the kit components selected from the group consisting of:

a) a master array comprising a support surface having a plurality of "address" oligonucleotide sequences immobilized thereon (e.g., directly or via respective linkers or "linking micro-beads"), the oligonucleotide sequences being immobilized in the form of a patterned, and optionally random, array;

b) a plurality of multi-ligand conjugates, each multi-ligand conjugate comprising a core having (preferably independently) attached thereto: (i) molecules of a first oligonucleotide binding domain, each molecule comprising an oligonucleotide sequence complementary to a particular address oligonucleotide sequence of the master array, (ii) molecules of a second oligonucleotide binding domain, each molecule comprising an oligonucleotide sequence complementary to a characteristic oligonucleotide sequence of a target nucleic acid sequence (e.g., a gene and/or gene fragment), and (iii) at least one molecule of a third (and preferably non-oligonucleotide) ligand, selected from the group consisting of a binding ligands and polymerizable groups (e.g., acrylic or vinyl groups);

c) an assay array support comprising a support surface for the replicate array, e.g., coated with attachment sites for the third ligand (such as, immobilized molecules of a corresponding binding partner specific for the third binding ligand); and d) an array reader for determining the location of address oligonucleotides on the master array and the presence of hybridized target nucleic acids on the assay array.

In yet another alternative embodiment, the present invention provides a method and system for directly preparing a replicable array in the form of a reusable nucleic acid array. In this embodiment, the surface to which the nucleic acid is immobilized is provided by an optical fiber array, the assay array support surface being provided by the distal ends of the fibers themselves. Optionally, and preferably, micro-wells are etched into the distal ends of the optical fibers.

In such an embodiment, a conventional optical fiber bundle can be adapted for use as a specific binding array biosensor system for detecting a variety of target nucleic acids in a sample. Commercial sources provide optical imaging fiber bundles comprising thousands (e.g., 3,000–100,000) of hexagonally packed, individually-coated optical fibers. Each fiber in the array carries its own, isolated optical signal from one end of the fiber to the other. Individual specific binding ligands can be bound to one end of each fiber and the other end is functionally connected to a optical signal analyzer (e.g., a CCD camera).

The assay end (containing specific-binding ligands) of the fiber bundle is exposed to a sample solution containing the unknown target and other necessary reagents (if any) of the optical assay system. The optical signal pattern is recorded and analyzed at the other end of the bundle, using the image analyzer system.

Applicant has found that oligonucleotide binding domains, complementary to target sequences, can be attached to the optical assay array support surface in any suitable manner, e.g., either directly or by means of reversibly or irreversibly bound linking molecules or micro-beads. In turn, the ultimate location of the oligonucleotide binding domains can be determined (e.g., by optical means and assay), preferably controlled (e.g., by the use of reusable address domains), and optionally replicated (e.g., by the use of reversible linkers).

In one preferred embodiment, the system comprises a plurality of multi-ligand conjugates, each multi-ligand conjugate comprising molecules of a) a first oligonucleotide binding domain adapted to bind with a corresponding address ligand, and b) a second oligonucleotide binding domain complementary to a characteristic oligonucleotide sequence of a target nucleic acid (e.g., a gene and/or gene fragment). The address ligands are immobilized onto the distal end of the master array, either directly, or by the use of a linker or micro-bead. The multi-ligand conjugates would then load each of the addressed fibers with a known analyte-specific ligand. The set of analyte-specific ligands on the fibers in the bundle can be changed at will.

In another embodiment, attachment of the oligonucleotide binding domain is accomplished using a micro-bead. In this embodiment, the micro-bead is prepared such that it is attached to the oligonucleotide binding domain. The micro-bead and binding domain are then attached to the assay array support surface. Attachment of the micro-bead can be accomplished using any suitable binding pair, such as, for example, avidin-biotin. In an alternative embodiment, photoreactive reagents can be used to attach the micro-bead to the assay array support surface.

Optionally, and preferably, the system further comprises an image analyzer. In this embodiment, the bundle of fibers is connected at one end to an optical sensor that collects signals and processes information from these multiple sensors (e.g., fibers).

In such an approach the invention provides a reusable nucleic acid array, in which the user is able to change the function of the nucleic acid array for each particular use. For example, the linker or micro-bead can be coated with iminobiotin, and the assay array support surface can be coated with biotin. The linker or micro-bead can thus be reversibly attached to the assay array support surface. The linker or micro-bead can be dissociated by altering the pH such that the lower pH causes the linker or micro-bead to dissociate with the assay array support surface.

In one embodiment, micro-wells can be etched into the distal end of each optical fiber using techniques known in the art. For example, a wet chemical etching procedure can be used to selectively etch the cores of the individual fibers. This technique takes advantage of the difference in etch rates between the core and cladding materials of the fiber. By controlling the etching time, those of skill in the art will appreciate the manner in which high-density, ordered micro-well arrays of known shape and well volume are obtained. Well architecture is determined by the preformed imagining fiber. Since each micro-well is contained at the end of its own optical fiber, each well can serve as an individual sensor. Preferably, the diameter of the etched micro-wells is slightly larger than that of individual linking micro-beads used in connection therewith.

In one embodiment, for instance, a solution containing a plurality of micro-beads having one or more oligonucleotide binding domains complementary to a target nucleic acid attached thereto is added to the surface of a bundle of optical fibers. The individual linking micro-beads randomly settle into each micro-well as the solution is allowed to evaporate from the optical fiber bundle surface. Optionally, and in the event a photoreactive compound is used in connection with this embodiment, the optical fibers are illuminated, to allow the linking micro-bead to photocouple to the surface of each optical fiber. Optionally, excess micro-beads are then washed from the surface of the fiber bundle.

For instance, immobilization of a bead or oligonucleotide binding domain onto the distal end of the fiber, within the micro-well, can be accomplished using photoactivatable compounds to form bonds with the well surface. In one embodiment, the well surface of the optical fiber is coated with a photoreactive siloxane reagent, and thereafter, a solution containing free (i.e., unbound) oligonucleotide binding domain is applied to the well surface. The solution is then illuminated, activating the photoreactive groups and causing bond formation between the oligonucleotide binding domain and well surface. Illumination is accomplished by passing activating light through the fiber into the well.

As discussed above, each individual fiber of the fiber bundle can be etched at one end to provide a concave receptacle for a micro-bead. A photoreactive organosiloxane reagent can be prepared by bonding a commercial organosiloxane reagent, such as aminopropyldimethyl methoxy siloxane, with a thermochemically reactive photoreagent, such as the acid chloride of benzoylbenzoic acid. The photoreactive siloxane reagent is reacted with the concave silicon oxide surface of the etched optical fibers in the image analyzer bundle. In an alternative embodiment, each micro-well is coated with X-avidin to create a surface that will react with biotin. In this embodiment, the micro-beads are coated with biotin or iminobiotin derivatives.

Preferably, the linking micro-beads are spherical, and of a diameter approximately equal to (or slightly less than) that of the individual optical fibers. The linking micro-beads of the present invention are fabricated from any suitable material, including, for example, glass, polystyrene, polyvinylbenzophenone, photopolysiloxane-coated glass. Preferably, the micro-beads have a specific gravity greater than that of water, and have a chemical composition that is subject to bonding with organic reagents.

The oligonucleotide derivatives can be synthesized according to published and commercially utilized methods, as described in more detail herein. The length of the oligonucleotide sequences are optimized for desired hybridization strength and speed (usually in the 20–50 nucleotide range). The oligonucleotide sequences are complementary to the chosen target nucleic acid.

The "address oligonucleotide" derivatives can be coupled to the epoxy-activated linking micro-beads for the optical fiber ends. In a preferred embodiment, for example, homogeneous silica spheres of approximately the fiber diameter are reacted with a commercial organosiloxane reagent containing a thermochemically reactive group (e.g., epoxy) useful for coupling to amine groups of the oligonucleotide derivatives in this invention. Glycidoxypropyltriethoxy siloxane is reacted with the glass micro-beads under published reaction conditions, to provide an epoxy-glass surface. The address oligonucleotide derivatives of this invention terminate with alkylamine groups on spacers to couple readily with the epoxy groups on the surface of the linking micro-beads.

The bundle of etched photoreactive optical fibers is exposed to a slurry of linking micro-beads (in sufficient number to provide at least one type of address oligonucleotide per fiber), each micro-bead having address oligonucleotide sequences immobilized on its surface. Preferably, one oligonucleotide binding domain is bound to each optical fiber well. In this embodiment, the master array is reusable. This slurry is comprised of approximately equal numbers of beads with each of the desired address oligonucleotide sequences. The number of beads providing oligonucleotide sequences is sufficient to provide a redundancy (at least 3-fold) of each target nucleic acid specific site. As the solvent (preferably aqueous) evaporates from the slurry pool on the photoreactive surface in the dark or dim light, the uniform-sized beads are left in the concave pockets at the ends of the ordered arrangement of fibers. The linking micro-beads providing oligonucleotide sequences are then "fixed" by illumination in the dry state to form carbon-carbon bonds between the photoreactive groups on the optical fiber surface and the organic groups (mostly oligonucleotides) on the address oligonucleotide beads. Excess micro-beads are rinsed from the system.

The resultant optical fiber bundle will have a stable and ordered arrangement of the oligonucleotides complementary to target nucleic acid sequences on one end of its fibers, and the locations of the oligonucleotide sequences can be then determined by conventional methods of fluorescent hybridization, comprising sequential addition of fluorescent-labeled, complementary sequences to the array, with rinsing and array reading between each addition, as discussed in detail herein.

In one preferred embodiment, complementary sequences are labeled with fluorophores. Fluorescent-labeled oligonucleotides complementary to each of the sequences are synthesized, each containing several (e.g., one of ten) different fluorescent compounds that can be distinguished from each other. Each oligonucleotide, therefore, has a known sequence and a known identifiable label. The several oligonucleotides, each having a different, known sequence complementary to an oligonucleotide sequence on the surface and one of a comparable number of distinguishable fluorophores, are simultaneously applied to the surface and hybridized at 55° C. for 30 minutes.

The surface is then rinsed and analyzed to identify the locations of each of the sequences. Another set of sequences is then hybridized to the surface and scanned to identify the second set of sequences. This process is continued until all of the locations are identified, after which the master array is stripped by immersing in boiling water for two minutes. It is then ready for use to detect the presence of target nucleic acids in a sample.

In use, the master array is exposed to a test solution containing a plurality of target nucleic acid sequences (e.g., genes and/or gene fragments). The test solution is labeled via a fluorescent label to permit visualization of the results. The test solution is incubated under conditions to allow the oligonucleotide binding domain to hybridize to the target nucleic acid contained within the sample. Unbound solution is then rinsed from the master array. The hybridized nucleic acid sequences are visualized using an assay array reader, such as that mentioned above from Molecular Dynamics.

The assay arrays are washed with phosphate buffered saline containing 0.05% Tween 20 (PBS/Tween), then blocked with hybridization buffer, which consists of 4×SCC (0.6 M NaCl, 0.06 M citrate, pH 7.0), 0.1% (w/v) lauroylsarcosine, and 0.02% (w/v) sodium dodecyl sulfate, at 55° C. for 30 minutes. A sample containing DNA having a sequence complementary to one of the immobilized oligonucleotide probes on the array is applied to the support surface of the fiber and incubated for one hour at 55° C. in a sealed hybridization chamber. The support surface is then washed with 2×SSC containing 0.1% SDS (sodium dodecylsulfate) for 5 minutes at 55° C., after which 50 fmole of a fluorescent-labeled detection probe that is complementary to another sequence on the target DNA is applied to the support surface and incubated for one hour at 55° C. The support surface is then washed with 2×SSC containing 0.1% SDS for 5 minutes at 55° C., followed by a wash with 0.1×SSC, then dried and the fluorescence pattern recorded by the image analysis instrument, e.g., an array reader (e.g., as commercially available from Molecular Dynamics).

One of skill in the art will appreciate that the present invention can provide a variety of oligonucleotide sequences in association with a particular fiber bundle. In one embodiment, for example, the fiber wells are coated individually with specific binding agents. In another embodiment, the fiber wells are coated simultaneously with a general binding agent (e.g., iminobiotin). In this embodiment, the fiber wells are loaded from a mixture of specific binding agent micro-beads each containing the complement to the general binding agent (e.g., X-avidin).

Optionally, the system further includes an array reader, e.g., an assay array reader such as that commercially available from Molecular Dynamics. The resultant assay array can be used in a conventional manner, e.g., the assay array can be read by a standard array reader, while the master array can be re-used to prepare more assay arrays by repeating some or all of the steps set forth above.

What is claimed is:

1. An apparatus for producing an assay array, the apparatus comprising:
   a) a master array comprising a support surface having a plurality of address ligands immobilized thereon in the form of a patterned array, wherein each address ligand comprises a nucleic acid sequence;
   b) a plurality of multi-ligand conjugates, each multi-ligand conjugate comprising a core having attached thereto: (i) at least one molecule of a first ligand binding domain, comprising a nucleic acid sequence selected to bind in a complementary manner with a specific address ligand of the master array but not with target nucleic acid sequences that may be present in a biological sample, (ii) at least one molecule of a second ligand binding domain, comprising a nucleic acid sequence selected to bind in a complementary manner with a specific target nucleic acid sequence that may be present in the biological sample, and (iii) at least one molecule of a third ligand, the third ligand comprising a binding ligand configured to bind the multi-ligand conjugate to a binding partner; and
   c) an assay array support comprising a support surface and a plurality of binding partners selected to bind the third ligand for attachment of the multi-ligand conjugates to the assay array support to form the assay array.

2. An apparatus according to claim 1, wherein the nucleic acids of the master array and the multi-ligand conjugates each comprise a synthetic oligonucleotide.

3. An apparatus according to claim 1 further comprising a linking agent, the linking agent providing attachment of the address ligand with the master array support surface.

4. An apparatus according to claim 3 wherein the linking agent comprises a micro-bead.

5. An apparatus according to claim 1 wherein the first ligand binding domain, second ligand binding domain and third ligand are independently attached to the core of the multi-ligand conjugate.

6. An apparatus according to claim 1 wherein the binding ligand comprises biotin.

7. An apparatus according to claim 1 wherein the assay array support is coated with attachment sites for the third ligand.

8. An apparatus according to claim 7 wherein the third ligand comprises a binding ligand, and the attachment sites comprise molecules of a binding partner specific for the third ligand.

9. An apparatus of claim 1, wherein the third ligand is a biotin-poly(alkyleneoxide) amine derivative and the binding partner is avidin.

10. An apparatus of claim 9, wherein the third ligand is a biotin-poly(ethyleneoxide) amine derivative formed by reacting an N-oxysuccinimide ester of biotin with a poly(ethyleneoxide) diamine.

11. An apparatus of claim 9, wherein the avidin is attached to the assay support through a photoreactive siloxane reagent.

12. An apparatus of claim 11, wherein the photoreactive siloxane reagent is formed by reacting aminopropyldimethylmethoxy siloxane with the acid chloride of benzoylbenzoic acid.

13. An apparatus comprising a transitory structure formed in a process of producing an assay array, the transitory structure comprising:
   a) a master array support;
   b) a plurality of address ligands attached to the master array support, wherein each address ligand comprises a nucleic acid sequence;
   c) an assay array support comprising a support surface and avidin attached to the support surface;
   d) a plurality of multi-ligand conjugates attached to the assay array support, each multi-ligand conjugate comprising a core having attached thereto:
      (i) a first ligand comprising a nucleic acid sequence bound in a complementary manner with a specific address ligand attached to the master array support but not with target nucleic acid sequences that may be present in a biological sample;
(ii) a second ligand comprising a nucleic acid sequence selected to bind in a complementary manner with a specific target nucleic acid sequence that may be present in a biological sample;
(iii) a third ligand comprising a biotin-poly(alkyleneoxide) amine derivative bound to the avidin attached to the assay support.

14. An apparatus of claim 13, wherein the third ligand is a biotin-poly(ethyleneoxide) amine derivative formed by reacting an N-oxysuccinimide ester of biotin with a poly(ethyleneoxide) diamine.

15. An apparatus of claim 13, wherein the avidin is attached to the support surface through a photoreactive siloxane reagent.

* * * * *

UNITED STATES PATENT AND TRADEMARK OFFICE
CERTIFICATE OF CORRECTION

| | | |
|---|---|---|
| PATENT NO. | : 6,514,768 B1 | Page 1 of 3 |
| APPLICATION NO. | : 09/240466 | |
| DATED | : February 4, 2003 | |
| INVENTOR(S) | : Guire et al. | |

It is certified that error appears in the above-identified patent and that said Letters Patent is hereby corrected as shown below:

Title page,
Item [73], Assignee, "Surmodics, Inc.," should read -- SurModics, Inc., --.

Column 4,
Line 36, "that can is a nucleic" should read -- that is a nucleic --.
Lines 55 and 56, "assay support" should read -- assay array support --.

Column 5,
Line 38, "invention provides a" should read -- invention provides a master array comprising a --.
Line 39, "array having immobilized" should read -- array support having immobilized --.

Column 7,
Lines 52 and 55, "array can be fabricated" should read -- array support can be fabricated --.
Line 61, "array is" should read -- array support is --.

Column 8,
Lines 6 and 8, "organosiloxane reagent." should read -- organosilane reagent. --.
Line 9, "siloxane)" should read -- silane) --.
Lines 42, 50 and 58, "array surface" should read -- array support surface --.
Line 52, "array surface." should read -- array support surface. --.
Line 65, "photosiloxane)" should read -- photosilane) --.

Column 9,
Line 58, "carbonhydrogen)" should read -- carbon-hydrogen) --.

Column 11,
Lines 54-55, "oligonueleotides can be provided" should read -- oligonucleotides can be provided --.
Line 57, "oligonueleotide" should read -- oligonucleotide --.
Line 67, "array by gravity" should read -- array support by gravity --.

Column 12,
Line 6, "organosiloxane" should read -- organosilane --.
Line 8, "siloxane," should read -- silane, --.
Line 12, "siloxane" should read -- silane --.
Line 58, "organosiloxane" should read -- organosilane --.

UNITED STATES PATENT AND TRADEMARK OFFICE
CERTIFICATE OF CORRECTION

PATENT NO. : 6,514,768 B1
APPLICATION NO. : 09/240466
DATED : February 4, 2003
INVENTOR(S) : Guire et al.

It is certified that error appears in the above-identified patent and that said Letters Patent is hereby corrected as shown below:

Column 13,
Line 61, "organosiloxane" should read -- organosilane --.
Line 66, "siloxane" should read -- silane --.

Column 15,
Line 49, "organosiloxane" should read -- organosilane --.

Column 16,
Line 41, "array include" should read -- array support include --.
Line 42, "array itself," should read -- array support itself, --.
Line 44, "assay support" should read -- assay array support --.
Line 45, "square $\mu$m." should read -- square cm. --.
Line 46, "array, in" should read -- array support, in --.
Line 50, "array is" should read -- array support is --.
Lines 53-54, "organosiloxane" should read -- organosilane --.
Line 61, "siloxane" should read -- silane --.
Line 66, "array." should read -- array support. --.

Column 17,
Line 1, "array" should read -- array support --.
Line 12, "array surface" should read -- array support surface --.
Line 45, "master array having a support" should read -- master array support --.

Column 18,
Lines 13, 20 and 23, "assay support" should read -- assay array support --.
Line 15, "support in a" should read -- array support in a --.

Column 19,
Line 22, "array; and" should read -- array support; and --.
Line 23, "an assay array support comprising" should read -- an assay array comprising --.
Line 32, "array," should read -- array support, --.

Column 20,
Line 44, "master array, either" should read -- master array support surface, either --.

UNITED STATES PATENT AND TRADEMARK OFFICE
CERTIFICATE OF CORRECTION

PATENT NO. : 6,514,768 B1
APPLICATION NO. : 09/240466
DATED : February 4, 2003
INVENTOR(S) : Guire et al.

It is certified that error appears in the above-identified patent and that said Letters Patent is hereby corrected as shown below:

Column 21,
Line 39, "photoreactive siloxane reagent," should read -- photoreactive silane reagent, --.
Lines 48 and 49-50, "organosiloxane" should read -- organosilane --
Lines 51 and 53, "siloxane," should read -- silane, --.
Line 64, "photopolysiloxane" should read -- photopolysilane --.

Column 22,
Line 12, "organosiloxane" should read -- organosilane --.
Line 16, "siloxane" should read -- silane --.

Column 24,
Lines 48 and 49, claim 12: "siloxane" should read -- silane --.

Column 25,
Line 9, "assay support." should read -- assay array support. --.

Column 26,
Line 7, "siloxane reagent." should read -- silane reagent. --.

Signed and Sealed this

Twenty-seventh Day of June, 2006

JON W. DUDAS
*Director of the United States Patent and Trademark Office*